United States Patent [19]

Heckmann et al.

[11] Patent Number: 5,000,920

[45] Date of Patent: Mar. 19, 1991

[54] DEVICE FOR THE HEAT TREATMENT OF GASEOUS TEST SAMPLES

[75] Inventors: Johannes Heckmann; Wolfgang Bather, both of Lubeck, Fed. Rep. of Germany

[73] Assignee: Dragerwerk Aktiengesellschaft, Lubeck, Fed. Rep. of Germany

[21] Appl. No.: 163,634

[22] Filed: Mar. 3, 1988

[30] Foreign Application Priority Data

Mar. 12, 1987 [DE] Fed. Rep. of Germany ....... 3707943

[51] Int. Cl.$^5$ .............................................. G01N 31/22
[52] U.S. Cl. ......................................... 422/60; 422/58; 422/87; 422/88; 436/124; 436/126; 436/155; 436/159; 436/167; 436/178; 436/181
[58] Field of Search .................... 422/55, 58, 59, 60, 422/83, 86, 87, 88; 436/124, 126, 155, 159, 167, 178, 181, 902

[56] References Cited

U.S. PATENT DOCUMENTS

| 3,746,512 | 7/1973 | Kamei et al. ............................ 436/132 |
| 3,879,503 | 4/1975 | Peterson ................................. 261/153 |
| 4,122,671 | 10/1978 | Armstrong et al. ............... 502/185 X |
| 4,294,583 | 10/1981 | Leichnitz ............................ 422/86 X |
| 4,300,910 | 11/1981 | Pannwitz ............................ 422/88 X |
| 4,591,399 | 5/1986 | van der Smissen et al. .... 252/186.1 X |

FOREIGN PATENT DOCUMENTS 2155178 9/1985 United Kingdom ................. 422/86

Primary Examiner—Robert J. Warden
Assistant Examiner—Jill Johnston
Attorney, Agent, or Firm—McGlew & Tuttle

[57] ABSTRACT

A heat treatment device for the conversion of gaseous test samples into constituents determinable by a detector provides the possibility of obtaining the desired pyrolysis products even during the sampling, then feeding them directly to the detector. The device has a small structural shape, and is able to be carried and used easily and operated independently of an external energy supply. The heat treatment device is connectable to a number of different detectors. A container 1 through which the test gas can flow is provided with a chemical filler 5, 7, 8 capable of an exothermic reaction, and with a starter 4 initiating the reaction.

17 Claims, 1 Drawing Sheet

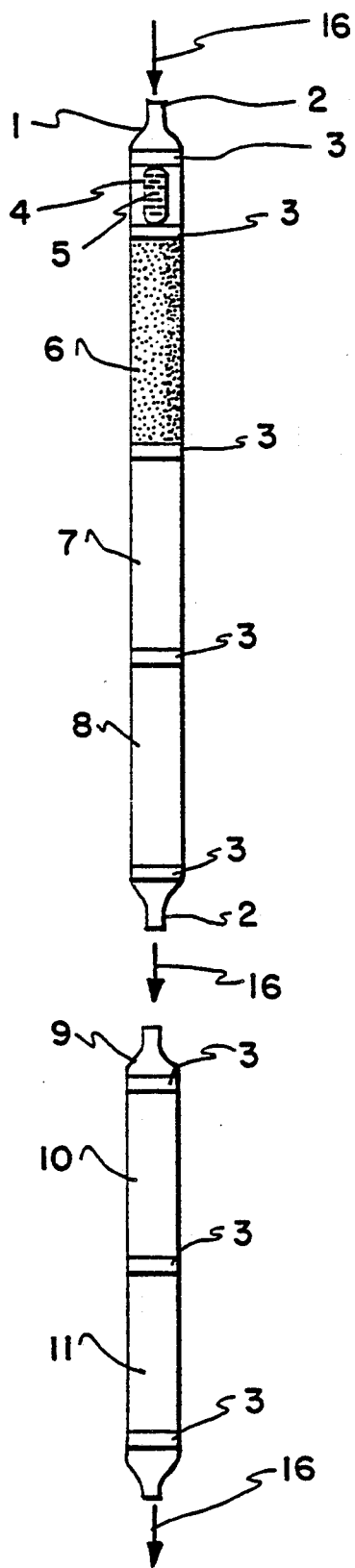
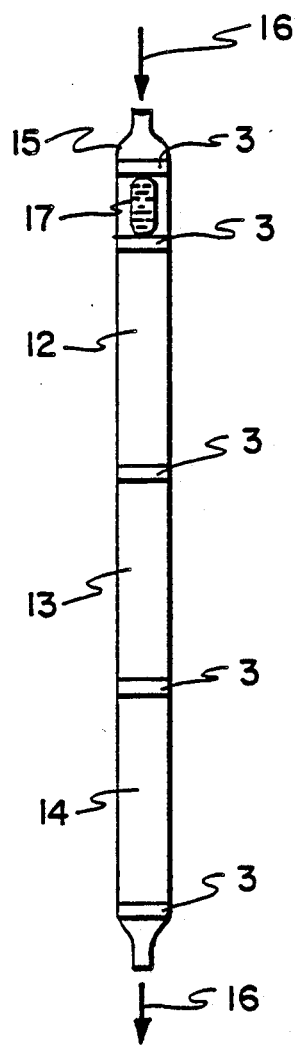

DEVICE FOR THE HEAT TREATMENT OF GASEOUS TEST SAMPLES

FIELD AND BACKGROUND OF THE INVENTION

This invention concerns a heat treatment device for converting gaseous test samples into constituents determinable by a detector.

The test samples to be studied, frequently taken from the ambient air, may contain pollutants to be determined. However, such samples may be unwanted substances such as those produced in chemical processes. For simplicity, reference will be made to the pollutants with the understanding that the test sample may also contain other unwanted substances.

Pollutants in the ambient air can be determined in various ways. A detector is necessary that responds to the specific pollutants to be studied. In many cases, it is impossible to provide an appropriately sensitive detector, or the detectors available are not intended for a specific pollutant, but are sensitive to several components likewise present in the ambient air to be studied.

This so-called cross-sensitivity makes reliable evaluation of the actual amount of pollutant difficult. Efforts are therefore made to increase the selectivity of a pollutant measurement, for example by resolving the pollutant to be determined into components to which the following detector reacts specifically and without cross-sensitivity. One such possibility consists of subjecting the pollutant to a heat treatment (pyrolysis), by which the pollutant is converted into the widest variety of pyrolyzates, one of which is determined by the detector.

Such a device with which a test sample to be studied is subjected to pyrolysis is described in German Patent Application Disclosure No. 21 35 203.

According to German Patent Application No. 21 35 203, the sample to be studied is passed through a collector provided with an adsorbent in which the pollutant to be determined is concentrated. After the sample, the collector is introduced into a separate analyzer. This instrument has a pyrolysis furnace in which the collector is heated, with the pollutant it contains being driven off and decomposed pyrolytically, and with a liberated pyrolyis product being studied by a following measuring instrument.

The known device is used to determine the content of alcohol in the breath, so that hydrogen as a typical pyrolysis product, which is fed through a filter permeable to hydrogen, such as palladium, to a hydrogen-measuring instrument such as an ionization chamber, for example, and is determined by the instrument. The measured concentration of hydrogen is thus a measure of the alcohol present in the breath sample.

The known device has the drawback that the air sample is first collected and then has to be subjected to pyrolysis. Different instruments must be used for the sampling and the pyrolysis, which requires a complicated procedure, and in addition, high energy consumption for the pyrolysis furnace as well as expensive measuring circuit for the detector. The requirement for electrical energy, both for the pyrolysis and for the measuring instrument, makes the method dependent on electrical supply systems or heavy, bulky units or batteries. Because of this, it is impossible to design a complete portable determination system that is both light in weight and easy to operate on the one hand, and on the other hand, requires the smallest possible amount of energy for operation.

Collecting the determinable pyrolysis products followed by measurement in one process directly during the sampling is impossible, but separate operating steps with intermediate steps of differing lengths are always necessary. An amount of pollutants that is not insignificant may remain adsorbed in the collector during the necessary desorption, which reduces the yield.

It is also possible to determine various pyrolysis products in the known device only when an appropriate permeable membrane is provided between the pyrolysis furnace and the measuring instrument.

SUMMARY AND OBJECTS OF THE INVENTION

The problem solved by the present invention is to provide, in a heat treatment device of the type mentioned, the desired pyrolysis products even during the sampling, then to feed them directly to the detector. It is an object of the invention to provide a device having a small structural shape, which may be easily carried and used, and which should be able to be operated independently of an external energy supply. Furthermore, the heat treatment device should be connectable to a number of different detectors.

According to the invention the above stated problem is solved by providing a container through which the test gas can flow with a chemical filler capable of an exothermic reaction and with a starter initiating the reaction.

The advantages produced by the invention lie essentially in the fact that a heat treatment device permitting pyrolysis or thermolysis is now held in a container through which the air sample can flow. This provides the advantages over a separate heat treatment device in the form of a furnace surrounding the container and filled with a chemical, that the test sample is decomposed immediately into its pyrolysis products after starting the exothermic reaction. It is not necessary to wait a long time for the heat transfer to take place from the furnace to the test sample. Since a number of pyrolysis products may be formed during the pyrolysis, these products can be determined subsequently by measuring instruments suitable for the purpose.

Because of the small structural shape that is possible, such a chemical heat treatment device pursuant to the invention can also be carried directly to the place of sampling with its detector and can also be used there. It is easy to start up, needs no external source of energy for operation, and is therefore simple to use, particularly without training. Tedious preparations for the transport of the collected test sample to a separate pyrolyzer and detector are also eliminated. High yields of pyrolysis products are obtained, since the test sample to be studied is decomposed pyrolytically on a large surface while flowing through the ignited chemical. Particularly in the study of low-boiling paint substances, the sampling, pyrolysis, and analysis can take place in one step. A preceding sample collection, hardly effective in this case, can be dispensed with.

A simple suitable embodiment of the chemical consists of a sodium monoxide filler that needs to be wet with a small amount of water to initiate the exothermic reaction, in order to produce the heat necessary for the pyrolysis while the test sample flows through.

A chemical filler that consists of a carrier that is coated with a readily oxidizable volatile substance that follows a catalyst filler for the conversion of the substance is likewise suitable. The volatile substance is removed from its carrier by introducing the test sample, and is fed to the catalyst, because of which it burns only as long as the test sample is also driven through the filler. Depending on the volatility of the selected substance, for example, either methanol of glycerin, intense or long-lasting gentle heating can be produced.

A beneficial arrangement can consist of silica gel or aluminum oxide being impregnated with methanol, or of the carrier being preceded upstream by a breakable ampoule filled with methanol, which is broken to initiate the reaction so that its contents are poured over the silica gel or aluminum oxide carrier, and its vapors burn on the following catalyst during the sampling. The heat liberated brings the catalyst to incandescence and thus it turns it into the mediator and reservoir of the pyrolytic heat.

A mixture of metal oxides known by the name of hopkalite has proved to be a suitable catalyst. In a desirable embodiment, an activated charcoal filler provided with Pt/Ir impregnation can be used as the catalyst. It has the advantage on the one hand that the activated charcoal carrier is also burned and the pyrolysis reaction thus continues, and on the other hand, the ignition process is initiated and maintained by the impregnation, and the pyrolysis is also catalytically promoted.

If pollutants of extremely low concentrations are to be measured, it is appropriate to design part of the chemical filler as a filler collecting the pollutant, which may be either an independent filler or the chemical itself. For example, such a chemical filler can be the activated charcoal filler itself. Resins of high polymers with adsorption activity are also suitable. In that case, the test sample is then first collected in the collecting filler and the chemical is ignited after completion of the sampling, so that the collecting filler is heated and the pyrolysis products are driven off by the chemical flowing through, and are fed to subsequent analysis.

Pyrophoric material that burns with the evolution of a substantial amount of heat, because of the atmospheric oxygen in the test sample introduced, can also be used beneficially as the chemical filler. A known example of a pyrophoric material is pyrophoric iron or mixtures of lead chromate and sulfur, potassium sulfate and carbon, or finely divided platinum black.

A substantial improvement of the pyrolytic action is produced by placing a follow-up catalyst beyond the chemical filler in the direction of flow. Its use for the conversion of the substance to be determined proves to be useful in particular when the burning time of the initially ignited chemical is not sufficient for a long-lasting sampling.

The follow-up catalyst can also be used to provide a higher heat of combustion than the preceding chemical filler is able to provide. Thus, the pyrolysis products that are formed in the chemical filler can be fed to another pyrolysis at elevated temperature, by which secondary products are formed in turn, which under some circumstances are more readily determinable than those formed at the beginning. A type of cascade connection of several heat treatment devices is thus obtained, with the follow-up catalyst in each case being ignited by the preceding chemical.

The follow-up catalyst suitably consists of activated charcoal provided with a platinum/iridium impregnation. In this case, for example, in a measurement of halogenated hydrocarbons, the pyrolysis products formed from the chemical would be shifted toward the formation of chlorine compounds, so that a chlorine-sensitive measuring instrument can be used as the detector. At the same time, the activated charcoal carrier can be caused to burn by the exothermic reaction of the preceding chemical filler, and can take over the continued production of heat and maintain the pyrolysis after the chemical is extinguished.

In the case of a cellulose follow-up catalyst, the pyrolysis products produced in the chemical filler are shifted toward the formation of hydrochlorides, so that a detector sensitive to hydrochloric acid can be used for the measurement.

The container of the heat transfer device suitably has the design of a tube in which the fillers are arranged in layers. This makes it possible to connect such a tube to a colorimetric test tube that is sensitive to a specific type of pyrolysis product. A multilayered test tube is thus obtained for the pyrolytic determination of pollutants, which is easy to handle and is usable everywhere. The following test tube in this case can either be integral with the heat treatment device designed as a preceding layer, or the two tubes can be produced separately and connected to one another as needed.

A special advantage is obtained by connecting the heat treatment device in front of a colorimetric band instrument, such as that disclosed by German Patent Application Disclosure No. 34 07 686, for example. This makes it possible to flush the colorimetric band with the specifically determinable pyrolysis products.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic representation showing the heat treatment device as a tube preceding a test tube, FIG. 2 is a schematic representation showing a second embodiment with the leading tube having a collecting layer.

DESCRIPTION OF THE PREFERRED EMBODIMENTS

Referring to the drawings, in particular the invention embodied therein comprises a container 1 or container 15 with a chemical filler 5, 7, 8, 12 or 14. The chemical filler is capable of reacting exothermically with a starter 2, 4 or 17 which initiates the reaction. The container 1 or 15 allows the passage of test gas such that test gas can flow through the container.

In FIG. 1, the container of a heat treatment device is shown in the form of a tube 1 preceding a following test tube 9. The leading tube 1 sealed at both ends can be opened at each end 2. The contents of the leading tube 1 are built up in layers, with the individual layers being separated from one another in each case by a permeable retainer 3. Following one another in the direction of flow of the test sample, which is indicated by the flow arrows 16, are first a breakable ampoule 4, then a silica gel filler 6 as the carrier, then a hopkalite filler 7 as catalyst, and finally a follow-up catalyst filler 8.

As an example, if halogenated hydrocarbons are to be determined with the test tube illustrated, the ampoule 4 filled with methanol 5 or glycerin is broken after opening the leading tube 1, because of which its contents pour over the silica gel filler 6 and this is saturated with the contents of the ampoule. When the test sample flows through with the gas to be determined in the direction of the flow arrows 16, the readily evaporating methanol impregnation is drawn through the following hopkalite filler 7 and ignites on contact with it. The heat liberated brings the hopkalite filler 7 to red incandescence. During the incandescence of the hopkalite filler 7, the halogenated hydrocarbon to be determined is decomposed pyrolytically into various constituents. The following catalyst filler 8 is ignited by the gas heated by the incandescent hokpalite, and in turn it burns at a temperature higher than the combustion temperature of the hopkalite filler 7. The catalyst filler 8 can consist of activated charcoal with a platinum/iridium impregnation, for example, so that the temperature of the catalyst filler 8 higher than that of the hopkalite filler 7 further increases the pyrolysis of the pollutant to be studied and thus provides an increased yield. At the same time, the equilibrium of the pyrolysis products is shifted in a desirable direction by use of the catalyst.

Thus, for example, when using an activated charcoal catalyst with a platinum/iridium impregnation, the pyrolysis reaction is shifted toward chlorine formation in the determination of chlorinated hydrocarbon, and toward hydrochloric acid formation when using a pure cellulose catalyst. Accordingly, detector tubes specifically sensitive to chlorine or hydrochloric acid can be connected to follow. Such a test tube 9 is shown in the flow connection with the leading tube 1. The pyrolysis products formed in the leading tube 1 are determined by this following test tube 9. This consists of a leading layer 10, which can be a drying layer, for example, and indicator layer 11. In the case of pyrolytic determination of chlorinated hydrocarbons, the determination tube can consist of a chlorine tube, if impregnated activated charcoal has been chosen as the catalyst filler 8, or it can consist of a hydrochloric acid determination tube when pure cellulose has been chosen as the catalyst filler 8.

The leading tube 15 opened at both ends shown in FIG. 2, in the direction of the flow arrows 16, first has a water ampoule 17 and an ignition layer 12, then a collecting layer 13, and finally a catalyst layer 14. All of the layers 12, 13, 14 are separated from one another by permeable and heat-resistant retainers 3.

The ignition layer 12 consists of sodium monoxide, which can be ignited by the addition of a small amount of water. The following collecting layer 13 is able to absorb and store the smallest amounts of pollutant to be detected before the subsequent pyrolysis is carried out. Compositions similar to those used in the leading tube 1 necessary according to FIG. 1 can be chosen as the catalyst layer 14.

To make a measurement, the test sample to be studied is caused to flow through the leading tube 15, with the pollutant to be determined being collected in the collecting layer 13. After a sufficiently long time of collection, the ignition layer 12 is ignited by breaking the water ampoule 17 and the pollutants collected in the collecting layer 13 are decomposed pyrolytically and fed to the following catalyst layer 14. Depending on the type of test gas to be studied and the pollutant contained in it, the collecting layer 13 can consist of activated charcoal or hopkalite. It is then used on the one hand to collect the pollutant to be determined, and on the other hand, as the catalyst layer 14 when pyrolysis is to be carried out The pyrolysis products formed can then be fed to a following test tube (not illustrated) and indicated by it, in the same way as shown in FIG. 1 and described in connection with it.

While specific embodiments of the invention have been shown and described in detail to illustrate the application of the principles of the invention, it will be understood that the invention may be embodied otherwise without departing from such principles.

What is claimed is:

1. A heat treatment device for converting gaseous test samples into constituents determinable by a detector, comprising: a container, through which test gas may flow, containing a chemical filler capable of undergoing an exothermic reaction, independent of the presence of gaseous test samples, generating sufficient heat to convert a test gas flowing through the container into constituents determinable by a detector and a starter capable of initiating the reaction of said chemical filler.

2. The heat treatment device according to claim 1, wherein: said chemical filler includes sodium monoxide which is wet by water to initiate the reaction.

3. The heat treatment device according to claim 1, wherein: said chemical filler includes a readily oxidizable, volatile substance which is applied to a carrier filler and a catalyst filler located adjacent to and in fluid flow communication with said carrier filler, the readily oxidizable volatile substance being brought into flow connection with said catalyst filler to initiate the reaction.

4. A heat treatment device according to claim 3, wherein: the carrier filler includes silica gel impregnated with methanol.

5. The heat treatment device according to claim 3, wherein: the starter is a breakable ampoule filled with methanol and positioned within said container and said carrier filler is positioned adjacent to and in fluid flow communication with said breakable ampoule for impregnation by the methanol upon breakage of the ampoule.

6. The heat treatment device according to claim 3, wherein: said catalyst filler includes hopcalite.

7. The heat treatment device according to claim 1, wherein: said chemical filler further includes a collecting filler for holding a test gas.

8. The heat treatment device according to claim 1, wherein: said chemical filler further includes pyrophoric material that is brought into fluid connection with ambient air through open ends of the container to initiate the reaction.

9. The heat treatment device according to claim 1, wherein: said chemical filler further includes platinum black that is brought into fluid connection with ambient air through open ends in the container to initiate the reaction.

10. The heat treatment device according to claim 1, further comprising: a follow-up catalyst positioned within said container adjacent to and in fluid flow communication with said chemical filler.

11. The heat treatment device according to claim 10, wherein: said follow-up catalyst includes one of pure activated charcoal and cellulose.

12. The heat treatment device according to claim 3, wherein: said catalyst includes an activated charcoal carrier, said activated charcoal carrier being provided with platinum/iridium impregnation.

13. The heat treatment device according to claim 1, wherein: said container is in the form of a tube, with fillers arranged in layers.

14. The heat treatment device according to claim 1, wherein: said container is adapted to be brought into fluid connection with a colorimetric test tube, the colorimetric test tube acting as a detector.

15. The heat treatment device according to claim 1, wherein: said container is adapted to be brought into fluid connection with a colorimetric band instrument as a detector.

16. A heat treatment device according to claim 13, wherein: the container and colorimetric test tube are formed as an integral tube wherein a layer containing a filler precedes the colorimetric test tube.

17. A heat treatment device for converting gaseous test samples by pyrolysis, into constituents determinable by a detector comprising a chamber having an inlet for test gas and an outlet and defining a test gas flow path along which a stream of test gas can flow from the inlet to the outlet and containing in the flow path a chemical filler capable of an exothermic reaction independent of the presence of gaseous test samples and a starter in the flow path adjacent to and in fluid flow communication with of the filler capable of initiating the reaction of said chemical filler at ambient temperature, whereby the test gas can be converted into constituents determinable by a detector by pyrolysis of the gas by heat generated by the exothermic reaction during flow of the gas through the reacting chemical filler.

* * * * *